United States Patent
Monstdt et al.

(10) Patent No.: US 7,323,000 B2
(45) Date of Patent: *Jan. 29, 2008

(54) DEVICE FOR IMPLANTING OF OCCLUSION SPIRALS

(75) Inventors: Hermann Monstdt, Bochum (DE); Hans Henkes, Essen (DE); Marion Denk, Bochum (DE)

(73) Assignee: Dendron GmbH, Bochum (DE)

( * ) Notice: Subject to any disclaimer, the term of this patent is extended or adjusted under 35 U.S.C. 154(b) by 834 days.

This patent is subject to a terminal disclaimer.

(21) Appl. No.: 10/129,426

(22) PCT Filed: Oct. 30, 2000

(86) PCT No.: PCT/EP00/10660

§ 371 (c)(1),
(2), (4) Date: Aug. 27, 2002

(87) PCT Pub. No.: WO91/13592

PCT Pub. Date: Sep. 19, 1991

(65) Prior Publication Data

US 2004/0078050 A1 Apr. 22, 2004

(30) Foreign Application Priority Data

Oct. 30, 1999 (DE) .............................. 199 52 387
Mar. 9, 2000 (DE) .............................. 100 10 840

(51) Int. Cl.
*A61M 29/00* (2006.01)

(52) U.S. Cl. ..................................... 606/200; 606/213
(58) Field of Classification Search .................. 606/1, 606/108, 151, 198, 213, 194, 200
See application file for complete search history.

(56) References Cited

U.S. PATENT DOCUMENTS

| | | | | | |
|---|---|---|---|---|---|
| 5,250,071 | A | * | 10/1993 | Palermo | 606/198 |
| 5,624,449 | A | * | 4/1997 | Pham et al. | 606/108 |
| 5,749,894 | A | * | 5/1998 | Engelson | 606/213 |
| 5,800,455 | A | * | 9/1998 | Palermo et al. | 606/191 |
| 5,941,888 | A | * | 8/1999 | Wallace et al. | 606/108 |
| 6,193,728 | B1 | * | 2/2001 | Ken et al. | 606/108 |
| 6,371,972 | B1 | * | 4/2002 | Wallace et al. | 606/200 |
| 6,533,801 | B2 | * | 3/2003 | Wallace et al. | 606/200 |
| 6,623,493 | B2 | * | 9/2003 | Wallace et al. | 606/151 |

* cited by examiner

Primary Examiner—Michael J. Hayes
Assistant Examiner—Michael Mendoza
(74) Attorney, Agent, or Firm—Berliner & Associates

(57) ABSTRACT

A device for the implantation of electrolytically severable occluding spirals in body cavities or blood vessels comprising a source of electrical power, a cathode, a catheter and an occluding spiral adapted to serve as an anode and able to slide in the catheter in the longitudinal direction, wherein the occluding spiral (3) is designed to be electrolytically corrodible at several spaced apart points so that when in contact with a body fluid one or more variably dimensioned lengths of the occluding spiral (3) may be severed by electrolysis.

34 Claims, 7 Drawing Sheets

DEVICE FOR IMPLANTING OF OCCLUSION SPIRALS

The invention relates to a device for the implantation of electrolytically severable occlusion spirals in body cavities or blood vessels.

The use of endovascular techniques for the occlusion of body cavities such as arteries, veins, fallopian tubes or vascular deformities such as for example vascular aneurysms is known in the art. The occlusion spiral is in this case usually introduced with the aid of an endovascular guide wire through a catheter into the cavity to be occluded and deposited therein.

The severance of the occluding spiral necessary for deposit thereof is in particular technically problematical, since the device required must on the one hand be as small as possible in design in order to be guided through the fine bore of the catheter to its destination, while on the other hand it must bring about a reliable severance of the occluding spiral, since otherwise on withdrawal of the catheter there might be an unintended removal of the occluding spiral from the cavity to be occluded and thus injury and/or rupture of the wall of the cavity or vessel.

Mechanical methods for the severance of occluding spirals from the insertion means do not take much time to perform but however the rigidity necessitated by technical features of the connection means between the occluding spiral and the introduction means impede the introduction of the implant. Furthermore, the low load carrying capacity of the connection due to its rigidity entails a not inappreciable risk of premature detachment of the insertion means from the occluding implant. Moreover, in the case of mechanical separation of the inserting wire and the occluding spiral, energy must be transmitted (as a rule by rotation of the inserting wire) and this may mean that the implant is dislodged out of the correct position.

The electrolytic severance of stainless steel wire ends during transcatheter electro-coagulation of blood vessels or deformities of the same was initially described in 1979 by Thompson et al. and by McAlister et al. (Radiology 133: 335-340, November 1979, AJR 132: 998-1000, June 1979).

Based on this method the European patent publication 0 484 468 described an occluding spiral involving the electrolytically corrodible design of the end of the guide wire at the connection between the guide wire and the occluding spiral. Although this device elegantly makes use of the voltage, applied to the occluding spiral serving as an anode for electro-thrombization, for the simultaneous severance of the wire end and the occluding spiral thereon, it does, just like the above mentioned mechanical severance method, suffer from the disadvantage that only implants of predetermined length can be detached or severed. It is therefore as a rule generally necessary for the length, that is to say the longitudinal extent, of the occluding spiral to be inserted, to be predetermined directly prior to the insertion of the implant on the basis of the size of the cavity to be occluded. Since the irregular form of body cavities to be occluded makes it difficult to correctly assess the length of the occluding spiral necessary for filling, there is the likelihood of excessively long or excessively short occluding spirals being introduced into the cavity to be occluded, something which may involve on the one hand an incomplete occlusion or on the other hand injury to or rupture of the wall of the cavity (or of contiguous vessels) to be occluded.

A further disadvantage of the electrolytic severance of the end of the guide wire is the fact that for production of the guide wire the only materials which can be utilized are those, which have a sufficiently high degree of strength to enable reliable guidance of the occluding wire through the guide wire. The selection of materials for forming the point of eventual electrolytic severance is consequently extremely limited.

In the case of prior art devices for the electrolytic severance of occluding spirals the latter and the guide wire are not produced integrally, but as a rule mechanically connected with each other. This design has the inherent disadvantage that in order to ensure sufficient strength in the proximal zone of the guide wire and for the purpose of rendering possible the electrolytic, corrosive severance of the wire end in the distal part of the wire the guide wire must be tapered toward its end in an involved grinding operation. This corrodible zone of the end of the guide wire at the connection between the guide wire and the occluding spiral must not, in order to ensure sufficient strength of the connection point, have a diameter below a certain minimum value of approximately 0.05 mm, since it is subjected to a high flexural load. The corrodible wire end representing the connection point between the occluding spiral and the guide wire is consequently extremely rigid and requires a relatively long time for electrolytic corrosive severance.

The German patent publication 4,445,715 C2 describes the severance of an occluding spiral from the insertion means by means of a laser beam directed or focussed on the point of severance of the implant using an entrained fiber light guide. This device renders possible severance of an optimum length of the occluding spiral in the course of an operation as needed for filling the cavity. Thus even in the case of the use of occluding spirals of uniform length this method renders possible the severance and deposit of a the length best suited for filling the cavity. The technology necessary for the application of this device is however presently extremely expensive.

Since the prior art does not at present offer any possibility, which is satisfactory as regards costs and safety for the endovascular deposit of occluding spirals with the respectively optimum length, one object of the invention is to make available a device, which makes it possible to deposit occluding spirals with the respectively appropriate length in body cavities or vessels in the most economic, effective and reliable manner.

This object is to be achieved in accordance with the invention by a device for the implantation of occluding spirals, which are able to be severed by electrolysis, in body cavities or blood vessels comprising a voltage source, a cathode, a catheter and an occluding spiral able to be slid in the catheter in the longitudinal direction and adapted to serve as an anode, which is characterized in that the occluding spiral is designed to be electrolytically corroded at a plurality of separate spaced points so that while in contact with a body fluid one or more variably dimensioned lengths of the occluding spiral may be severed by electrolysis. The integration of a plurality of electrolytically corrodible points in the occluding spiral offers the advantage over conventional systems for the electrolytic severance of occluding spirals, that during an implantation operation it is not only one but several lengths of the same spiral which may be severed in sequence and placed in the cavity to be occluded. This economizes not only as regards costs and time but also furthermore serves to further minimize surgery risks.

The invention is based on experiments of the inventors which showed that on the application of a current to a device in accordance with the invention there was the surprisingly specific effect of severance, at the electrolytically corrodible point, which is next to the distal end of the catheter, of the occluding spiral by electrolysis. This specifity is probably due to the fact that on the one hand the electrolytically corrodible points on the occluding spiral in the catheter are insulated by the same from the ionic medium and thus cannot be subject to electrolysis and on the other hand current density deceases in the proximal-distal direction owing to the distally increasing resistance in the occluding spiral. The electrolytically corrodible point which, considered in the distal direction, is closest to the distal end of the catheter, is consequently subjected to the most intensive electrolytic process and is preferentially dissolved.

The device of the invention for the implantation of occluding spirals combines, unlike any prior art device, the advantages of efficient occlusion with low surgery risk and economy. The implant length, which may be set during the implanting procedure, excludes the possibility of an insufficient length of occluding spiral being placed in the cavity to be occluded, which would lead to a thrombus of insufficient size for the space to be occluded. Furthermore it is possible to prevent the insertion of an excessively long occluding spiral for the cavity to be occluded, this meaning that the danger of injury or rupture of the cavity to be filled or of adjacent tissues is minimized. Moreover in the case of electrolytic severance of occluding spirals it is a question of a well tested technique, whose parameters are substantially laid down. Lastly, the device of the invention for the implantation of occluding spirals does offer the advantage of the possibility of using standard lengths of occluding spiral suitable for mass production. This constitutes a price advantage over occluding spirals of set length employed in conventional electrolytic or mechanical severance, because in contradistinction thereto occluding spirals of different length have to be made up, which then in the implantation operation are installed as a whole by severance of the wire end in the cavity to be occluded.

Since the electrolytically corrodible points of the device in accordance with the invention constitute a part of the occluding spiral itself and furthermore are present in plural number, they are subject to substantially lower bending forces during the implantation operation than conventional rigidly designed electrolytically formed connections between the guide wire and the occluding spiral. This low flexure load renders possible the use of electrolytically corrodible points with a substantially smaller diameter than in the prior art, this meaning an improved and more rapid electrolytic severance of the occluding spiral. Such small diameters of under 0.5 mm are able to be achieved by mechanical methods for example.

A further advantage of the design of the electrolytically corroding points in the device of the invention in the occluding spiral itself over the prior art method of severance of the guide wire end is the resulting substantially wider choice of materials able to be employed for forming the corrodible severance points. Unlike conventional severance of the guide wire end the electrolytically corrodible points provided in the occluding spiral in the device of the invention do not have to be particularly robust so that it is possible to utilize less robust, more flexible materials providing same are corrodible and compatible with the body.

It is convenient for an insertion means in the form of a guide wire to be provided proximally adjacent to the occluding spiral. Such a design offers the advantage of being able to manufacture the guide wire of materials lower in price than the occluding spiral material, more particularly because it does not come into contact with body tissues. Moreover, the structure of the guide wire is preferably such that good control of the occluding spiral by the catheter is possible, this meaning improved placement.

In the case of such a design of the device of the invention insertion means and occluding spiral are preferably joined together by soldering and/or brazing and/or bonding and/or welding operations and/or by mechanical connections. It is here a question of methods of connection known in the prior art, which are characterized by simplicity and strength of the connection so produced.

In a further embodiment it is possible for the guide wire and the occluding spiral of the device in accordance with the invention to be formed as parts of the same wire. This embodiment is characterized by being particularly robust and may be low in price, since the above mentioned step of connecting the guide wire to the occluding spiral is dispensed with.

In accordance with a particularly advantageous embodiment of the device of the invention the occluding spiral or a part thereof are in the form of a micro-spiral. This design offers the advantage that a greater area is available for thrombosing. For the same purpose it is also possible for other designs of the occluding spiral to be employed, which increase the area of the same and for example designs would be possible, whose distal end is forked.

In order to ensure the gentlest and most effective filling of the cavity to be occluded, a design of the device in accordance with the invention is advantageous, in the case of which the occluding spiral or a part thereof is subject to an elastic biasing force so that after release from the catheter coils are formed by it. This design renders possible a dense and safe filling of the cavity to be occluded without the occluding spiral having to be shaped by the wall of the cavity to be occluded for the formation of such coils, something which reduces the risk of rupture of the wall. In this case the elastic stress causes the formation of secondary coils.

It is convenient for the electrolytically non-corrodible sections of the occluding spiral to contain one or more of the following materials: noble metals or noble metal alloys, corrosion-resistant ceramic materials, corrosion-resistant plastics, and preferably platinum metal alloys.

Also preferred is an embodiment of the device of the invention whose occluding spiral comprises, at the electrolytically corrodible points, one or more of the following materials: ceramic materials, plastics, base metals or alloys thereof, and preferably stainless steel.

In this respect stainless steels of the types AISI 301, 303 or 316 or, respectively, subgroups of these types, are suitable.

The ceramic materials and plastics employed for forming the occluding spiral are electrically conductive.

In accordance with an advantageous embodiment for forming the electrolytically non-corrodible sections at transitions with the electrolytically corrodible points combinations of materials are selected which are suitable for forming local elements. It is in this manner that—independently of the reduction in diameter at the corrodible points—the electrolytic severance of the occluding spirals is improved.

In this respect the most suitable material combinations are those in which for forming the electrolytically corrodible points stainless steels, preferably of the type AISI 301, 304, 316 or subgroups thereof, Ti or TiNi alloys, or Co based alloys with one or more of the following noble metals or, respectively, noble metal alloys: Pt, Pt metals, Pt alloys, Au alloys or Sn alloys, are present.

The use of the above mentioned materials for the formation of the electrolytically non-corrodible sections and of the electrolytically corrodible points of the occluding spiral ensure specific electrolytic corrosion of the occluding spiral at the predetermined points.

It is particularly convenient to form electrolytically corrodible points which constitute local elements on either side. This embodiment of the electrolytically corrodible points is substantially more susceptible to corrosion and therefore corrodes substantially more rapidly than electrolytically corrodible points, which only form a local element on one side. Consequently it is preferred to utilize material combinations as far as possible apart in the electrochemical series. This as well is an advantage of the device in accordance with the invention over the prior art systems, which corrode the end of the guide wire for severance of the embolizing wire, since in this case it is merely to one side, namely on the embolizing wire side, that a local element is formed, the embolizing wire being as a rule a platinum wire.

The configuration of the electrolytically corrodible point is conveniently determined in accordance with functional aspects. Thus having regard to the flexural load it is an advantage to adapt the form of the electrolytically corrodible points to the form of the occluding spiral and to integrate same for example in the coils or turns of an occluding spiral designed in the form of a micro-spiral. On the one hand an essentially straight form of the electrolytically corrodible points does offer the advantage of being simpler technically. For the purpose of facilitating sliding of the occluding spiral in the catheter it is advantageous to have an alignment of the essentially straight electrolytically corrodible points of the occluding spiral on the longitudinal axis of the occluding spiral.

The electrolytically corrodible points on the occluding spiral may here for example be constituted by fittings, which are placed between the electrolytically non-corrodible fractions of the occluding spiral. This embodiment possesses the advantage that in this case a particularly large number of different materials may be combined with one another for the formation of the electrolytically corrodible points and the electrolytically non-corrodible sections. This embodiment is furthermore advantageous because the electrolytically corrodible points and the electrolytically non-corrodible sections may be modularly joined together, that is to say in a technically simple fashion, for the formation of occluding spirals of variable length. This is particularly simple when the electrolytically corrodible points and accordingly the fittings constituting same are made essentially straight.

It is convenient for the fittings constituting the electrolytically corrodible points to be connected with the non-corrodible sections by soldering and/or brazing and/or bonding and/or welding operations. By the same token it is possible for the fittings constituting the electrolytically corrodible points to be mechanically joined with the electrolytically non-corrodible sections, for example by clamping or crimping in position, if the electrolytically non-corrodible sections possess recesses to receive such fittings. This is for instance the case with electrolytically non-corrodible sections, which are formed by micro-spirals encircling an inner cavity. The fittings may be thus inserted in an interlocking manner in such cavity and fixed inside it. Then it is furthermore advantageous for outer part receiving the fittings, of the electrolytically non-corrodible sections in the form of micro-spirals to be reinforced.

It is in this respect more especially advantageous for the fittings constituting electrolytically corrodible points to be pre-corroded by etching or other methods so that the diameter thereof tapers toward the middle. The outer or, respectively, weakened fractions of the fittings with a larger diameter are then joined to the electrolytically non-corrodible sections by non-autogenous welding for example, mechanical insertion or bonding. The connection between the electrolytically corrodible points and the electrolytically non-corrodible section is therefore extremely robust, whereas the diameter, which tapers owing to pre-corrosion toward the middle of the mold, favors satisfactory electrolytic severance of the occluding spiral. In this respect, in the case of platinum alloys or platinum metals as a material combination for the formation of the electrolytically non-corrodible sections with stainless steel as a material for the fittings constituting the electrolytically corrodible point, joining by non-autogenous welding is particularly preferred. For the man in the art it is clear that the possibility of pre-corrosion of the electrolytically corrodible points is also possible, if same are not constituted by fittings.

In this respect it is convenient to provide the fittings with a partial coating of a material, which is higher up in the electrochemical series than the material constituting the fittings. This embodiment is particularly advantageous as regards their corrodibility of the electrolytically corrodible points which are placed at positions, where the fitting is devoid of coating. Coatings of Zn or Sn or, respectively, alloys such metals on fittings of stainless steel have been found to be particularly satisfactory here.

The mechanical application of the fittings is in this respect particularly advantageous, if the electrolytically corrodible points are to be made substantially straight and to be arranged along the longitudinal axis of the occluding spiral. The fitting together of the modules constituting the occluding spiral (non-electrolytically corrodible sections and the electrolytically corrodible points) is in this case particularly simple technically.

For even better holding and stabilizing of the individual modules constituting the occluding spiral it is also possible to adopt a combination of the above mentioned methods.

The flexibility of the occluding spiral is also ensured in the case of mechanical fitting together by the selection of material and owing to the small diameter of the fittings constituting the electrolytically corrodible points.

In one embodiment of the device in accordance with the invention the fittings constituting the electrolytically corrodible points are designed as micro-system components. The same may for instance be designed as elongated micro-system components, whose diameter tapers toward the middle. The insertion of the micro-system components is performed using the said conventional methods. The use of such micro-system components tapering toward the middle has here the advantage that areas with the largest diameter may be fitted to the electrolytically non-corrodible sections and accordingly ensure a firm connection between the parts. The tapering area with a smaller diameter is on the other hand exposed to the surrounding medium and may readily be corroded electrolytically. It is in this manner that the electrolytically corrodible points may be produced with a particularly small diameter.

The taper in diameter of the electrolytically corrodible points toward the middle is expedient for other designs of the electrolytically corrodible points as well as regards satisfactory corrodibility.

In another embodiment of the device in accordance with the invention the occluding spiral or a part thereof contains a continuous wire core of electrolytically corrodible material, which is surrounded by a casing of electrolytically corrosion-resistant material interrupted along its longitudinal axis at spaced points. The guide wire and the core of the occluding spiral are here preferably parts of the same wire.

This embodiment is particularly economic, because on the one hand the welding, soldering, brazing or bonding operation for connection of the occluding spiral and the insertion means is no longer necessary and on the other hand the wire core will consist of electrolytically corrodible material which as a rule is cheaper than the electrolytically non-corrodible materials, whereas only small quantities of material, which is less electrolytically corrodible than the wire core, may be utilized for coating.

The diameter of the occluding spiral in the device of the invention is in this case preferably so selected that on the one hand it is sufficiently robust and on the one hand the electrolytically corrodible points are able to be corroded in situ in a satisfactory manner electrolytically. In this respect it is an advantage to have an embodiment with diameters at electrolytically corrodible points of the occluding spiral between 0.01 and 0.05 mm and preferably 0.02 and 0.04 mm and more especially of 0.03 mm. The electrolytically non-corrodible sections of the occluding spiral may on the other hand have larger diameters.

In a further advantageous embodiment the end of the guide wire is insulated for example by a material coating with reduced corrosion properties or a shrunk on sleeve, so that it is not subject to electrolytic corrosion.

The preferred application of the device of the invention is in veterinary or human medicine and more particularly for the endovascular treatment of intracranial aneurysms and acquired or innate arteriovenous blood vessel deformities and/or fistulas and/or for the embolization of tumors by thrombozation.

The invention will now be described by way of example in the following with reference to the drawings showing working embodiments.

FIG. 1 shows a vertical section taken through a micro-spiral 3 positioned in a sacculated aneurysm together with the device employed therefor magnified several times.

FIGS. 1b and 1c show the part 15 viewed in FIG. 1 on a larger scale at the electrolytically corroded point 14 of the micro-spiral 3 which is illustrated in two possible designs thereof.

FIGS. 2a and 2b show, on a larger scale than in FIG. 1, three possibilities for the arrangement of the electrolytically corrodible points 11 and of electrolytically non-corrodible sections 10 in the micro-spiral 3 in accordance with the invention.

FIGS. 3a through c show on a larger scale than in FIG. 1, three possibilities for the arrangement of electrolytically corrodible points 11 and of electrolytically non-corrodible sections 10 in the micro-spiral 3 of the invention with electrolytically corrodible points 11 arranged along the longitudinal axis of the micro-spiral 3

Figure 1:
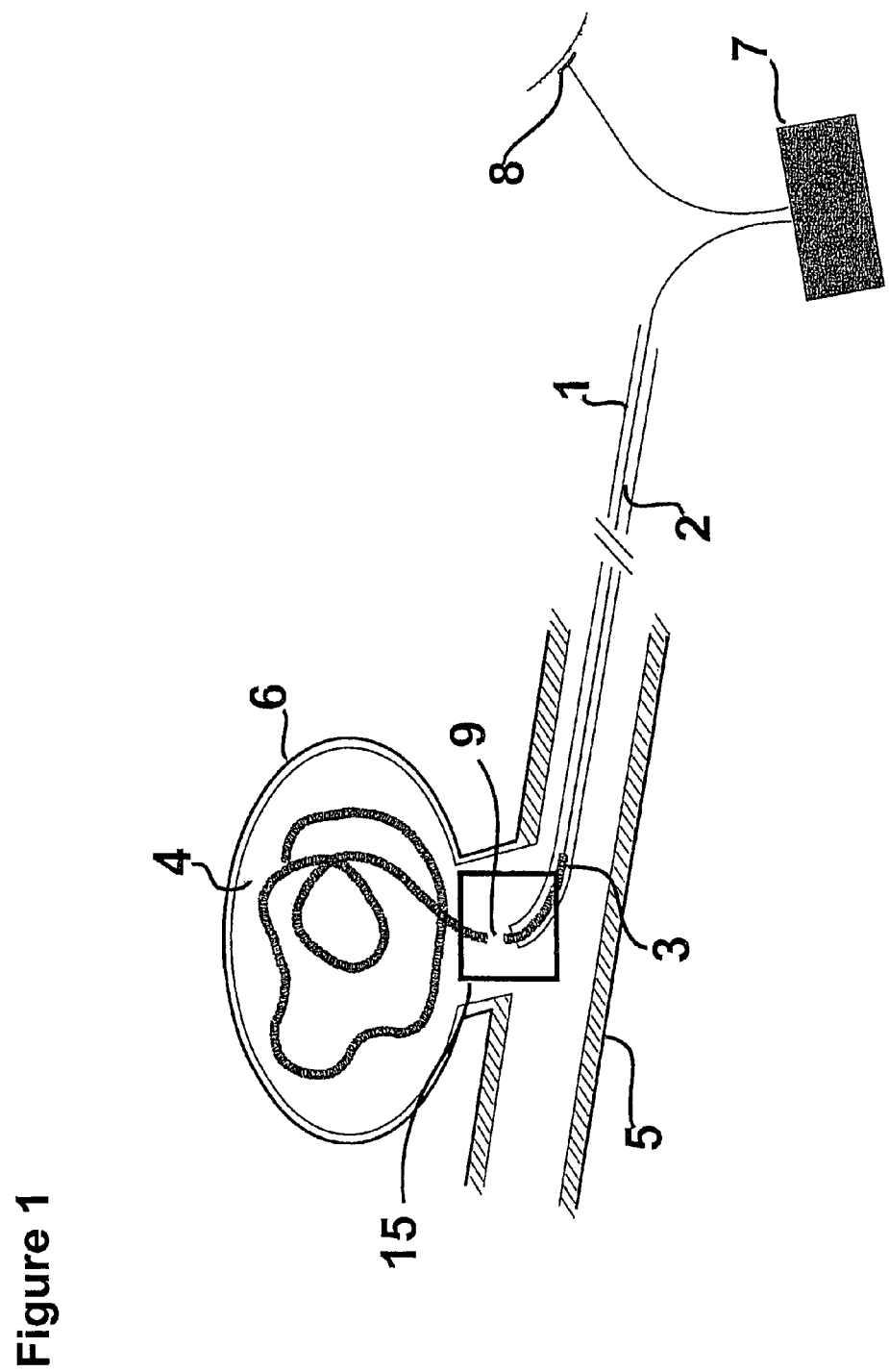

FIG. 1 shows a catheter 1 and more particularly a flexible micro-catheter. An occluding spiral 3, which is manufactured of platinum metal alloy, in the form of a micro-spiral is provided with electrolytically corrodible points 11 of stainless steel, and is positioned with the aid of the guide wire 2 at the mouth of the aneurysm 6 through the micro-catheter, said guide wire 2 being joined by a welding technique to the micro-spiral 3. Since this connection produced by non-autogenous welding between the guide wire 2 and the micro-spiral 3 is not intended for electrolytic severance of the micro-spiral 3 and accordingly does not have to have a particularly small diameter, it is particularly robust.

The use of stainless steel and platinum for the design of the guide wire on the one hand and, respectively, of the occluding spiral on the other hand is here particularly advantageous, since the nickel comprised in the steel is joined to the platinum in the course of welding to form an extremely smooth and robust connection with the platinum. By sliding the guide means 2 in the distal direction along the longitudinal axis of the micro-catheter the micro-spiral 3 is introduced into the aneurysm 6 and owing to its elastic biasing forms secondary coils or turns 4 on leaving the micro-catheter. Owing to possibility of longitudinal sliding of the guide wire 2 and of the micro-spiral 3 in the micro-catheter 1 a length of the micro-spiral 3, which individually is adapted to the volume of the cavity to be filled, is introduced into the cavity. Following this with the aid of a source 7 of electrical power a voltage is applied for 0.1 to 20 minutes to the cathode 8, positioned on the body surface, and to the micro-spiral 3, which is placed in the aneurysm 6 which is to be occluded and acts as an anode. This leads to electrolytic severance of the part, located in the blood, of the micro-spiral 3 at the electrolytically corrodible point 9 which is next to the distal end of the catheter. FIG. 1 represents a micro-spiral 3, whose electrolytically corrodible point 9, which is closest to the distal end of the micro-catheter 1 is already electrolytically corroded.

Figure 1B:
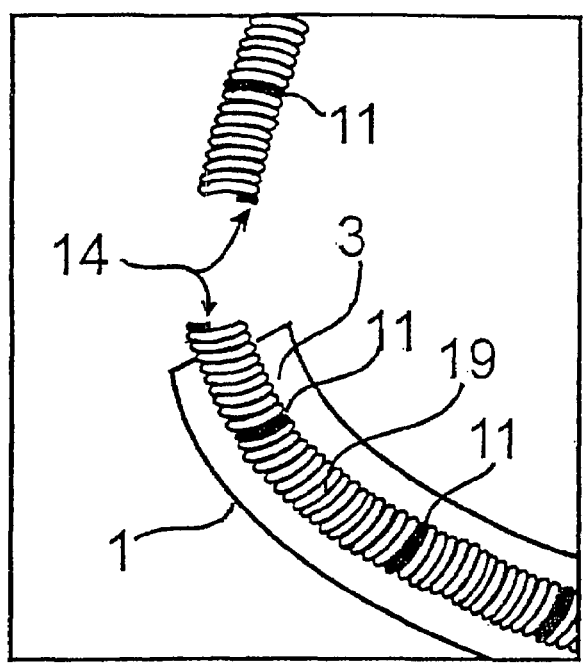

FIG. 1b is a larger view of part of FIG. 1 to indicate the electrolytically corrodible point, which is next to the distal end of the micro-catheter 1, in the corroded state 14. Further electrolytically corrodible points 11 located in the blood or still located in the micro-catheter on the other hand are still intact. The electrolytically corrodible points are adapted to the shape of the micro-coils 19 of the micro-spiral.

Figure 1C:
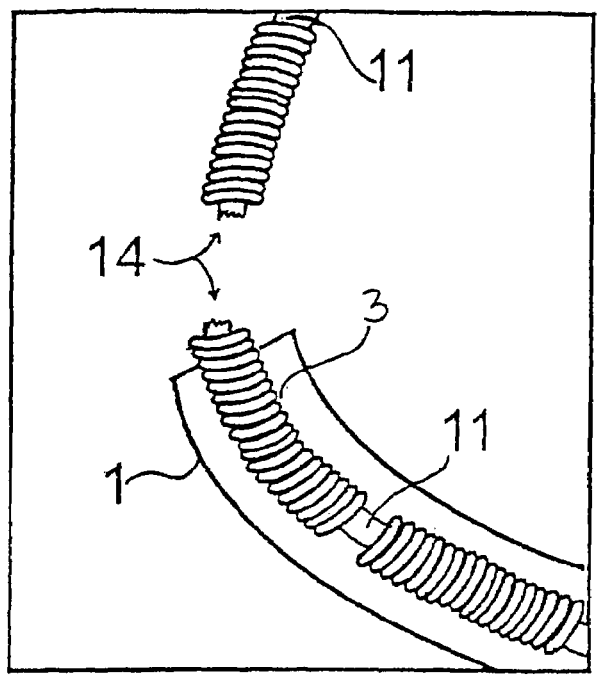

FIG. 1c is also an enlarged view of part of FIG. 1 indicating the electrolytically corrodible point, which is next to the distal end of the micro-catheter 1, in the corroded condition 14 for a micro-spiral 3 with essentially straight electrolytically corrodible points 11, which are aligned with the longitudinal axis of the micro-spiral.

Figure 2A:
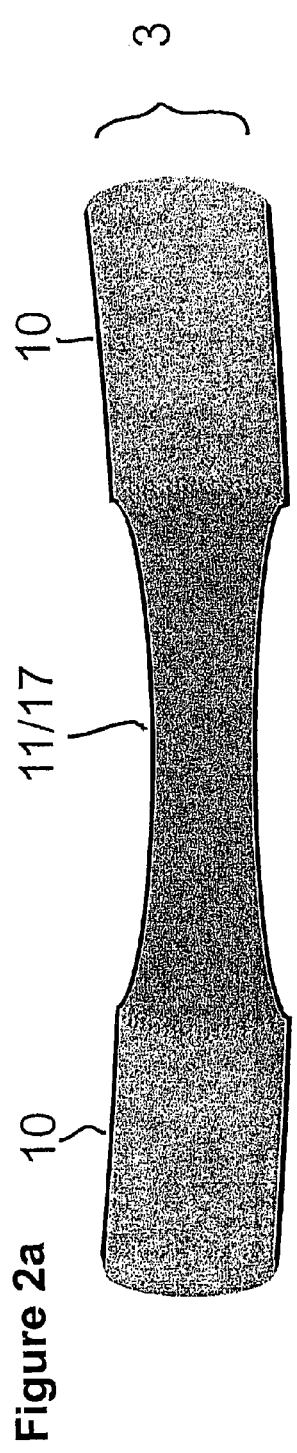
Figure 2B:
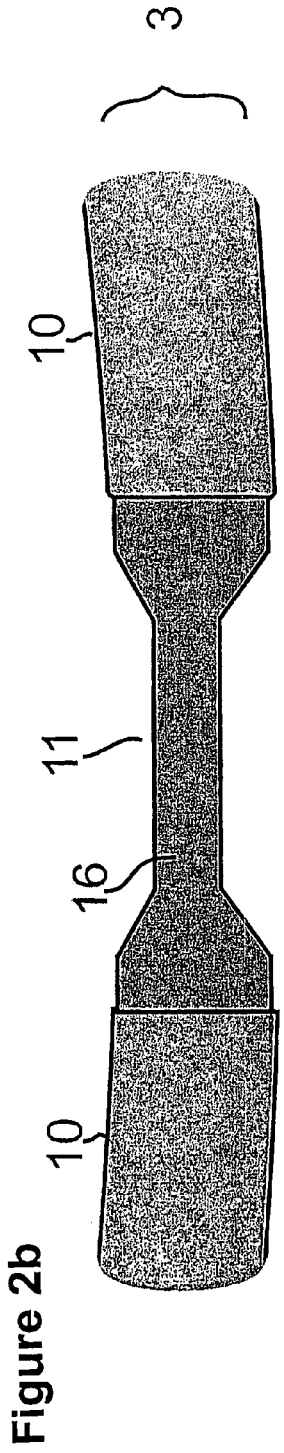
Figure 2C:
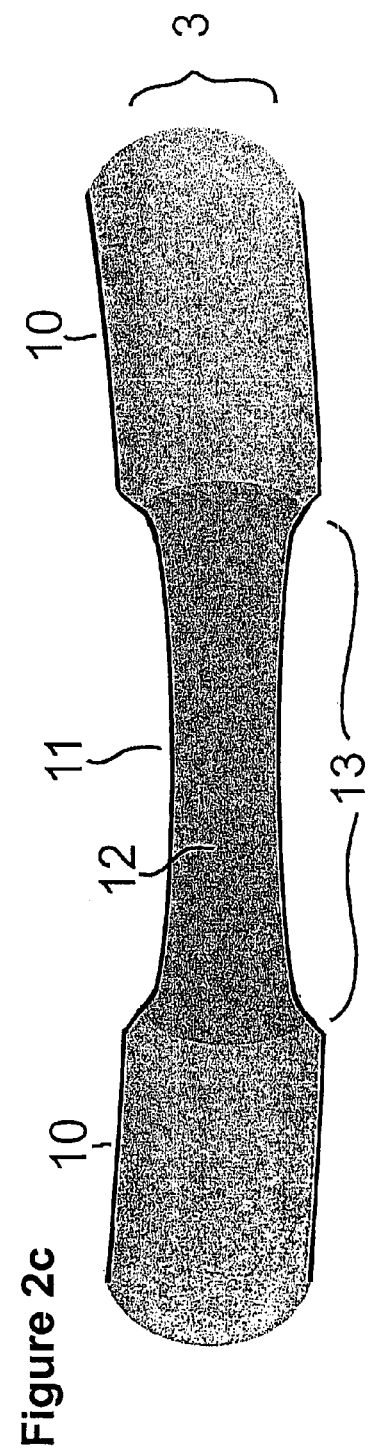

FIGS. 2a through c show, on a scale larger than in FIG. 1, a section of three different embodiments of the micro-spiral 3 in accordance with the invention.

FIG. 2a shows a micro-spiral 3 having non-corrodible sections 10 of a platinum alloy, to which a stainless steel fitting 17, having a diameter of 0.03 mm and constituting an electrolytically corrodible point 11 has been joined by welding. FIG. 2b shows a part of a micro-spiral 3 in accordance with the invention with a micro-system component 16 as an electrolytically corrodible point 11, which is fitted by bonding between the electrolytically non-corrodible sections 10.

FIG. 2c shows a part of a micro-spiral 3 comprising a noble metal core 12 of 0.03 mm in diameter. This noble metal core 12 is surrounded by a coating of an electrolytically corrosion resistant material 13, which is provided with interruptions at regular intervals, at which the noble metal core is accessible from the outside and accordingly forms an electrolytically corrodible point 11.

Figure 3A:
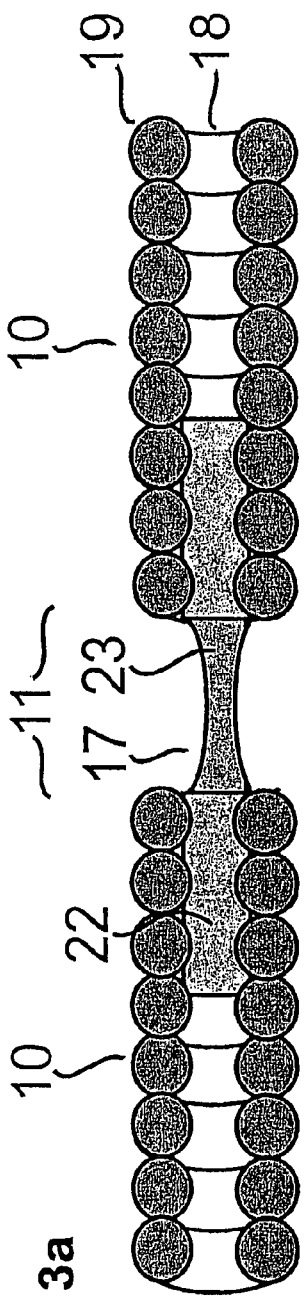
Figure 3B:
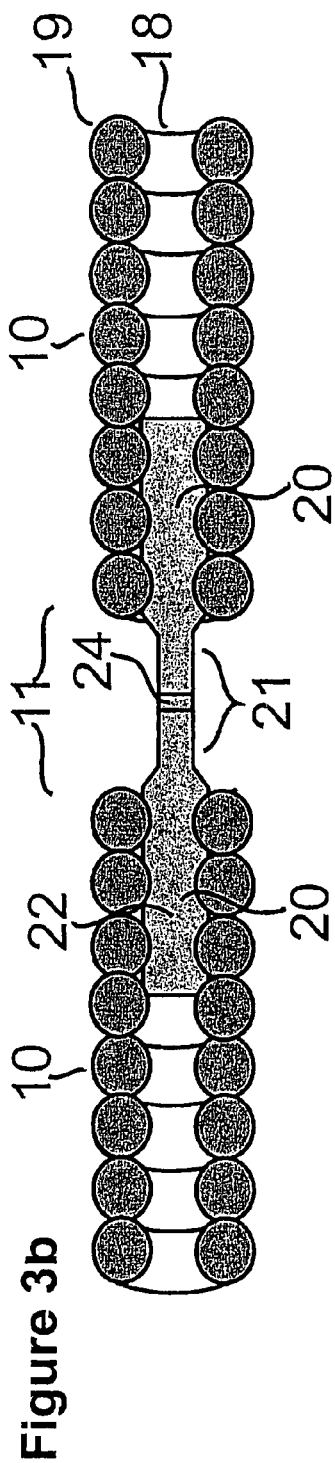
Figure 3C:
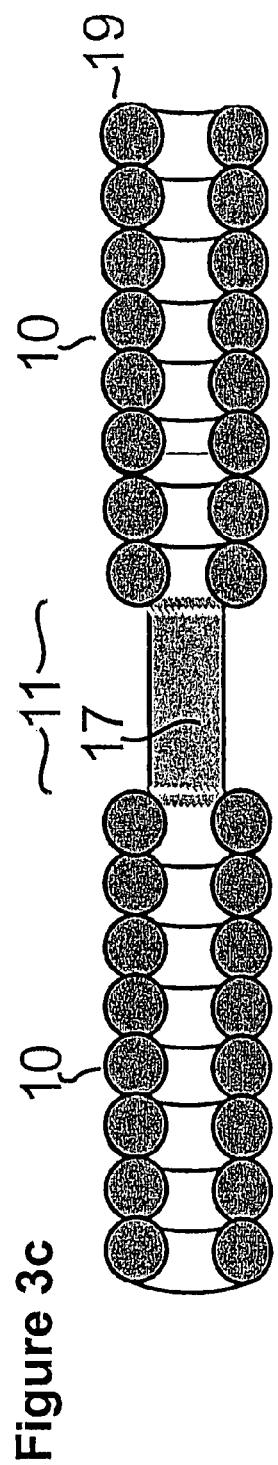

FIGS. 3a through c are views, on a larger scale than in FIG. 1, of three different embodiments of the micro-spiral 3 of the invention having electrolytically corrodible points 11 arranged along the longitudinal axis of the micro-spiral 3.

FIG. 3a shows a micro-spiral 3 having a substantially straight fitting 17 of stainless steel, which is fitted in an interlocking fashion in the interior space 18 of the micro-coils 19 of platinum wire. The modular concatenation of electrolytically non-corrodible sections 10 of platinum micro-coils 19 and of essentially straight fittings 17 means that at regular intervals, where the essentially straight fittings 17 are not surrounded by the platinum micro-coils 19 and are thus accessible from the outside, electrolytically corrodible points 11 are formed. The electrolytically non-corrodible sections 10 of the micro-spiral 3 are on the other hand formed by the platinum wire wound into micro-coils 19 and is fitted around the essentially straight noble metal fittings 17 in a mechanically interlocking manner on either side. The fitting 17 is surrounded by an Sn layer 22, which is removed in the middle owing to pre-corrosion. Consequently the pre-corroded middle part 23, which constitutes the electrolytically corrodible point 11, of the fitting 17 is particularly accessible to electrolytic corrosion, since it has a particularly small diameter and forms local elements on both sides owing to the Sn coating.

FIG. 3b also shows a modularly designed micro-coil 3, within which the micro-coils 19 of the platinum wire are fitted in an interlocking manner around the ends of a micro-system component 16, manufactured of stainless steel, and thus form the electrolytically non-corrodible sections 10, between which the exposed sections of the micro-system component 16 form the electrolytically corrodible point 11. The insertion of the sections of the micro-system component 16 with a larger diameter 20 in the inner space 18 of the platinum wire coils 19 ensures a firm fixation of the modular elements together. The design of the electrolytically corrodible point 11 in the form of the tapered section 21 of the micro-system component 16 with a smaller diameter 21 on the other hand renders possible a larger degree of flexibility and the advantage of good corrodibility of the electrolytically corrodible point 11.

This corrodibility is enhanced by the design of the micro-system component, which to a major extent consists of an Sn alloy 22 and only contains a micro-severance element 24 in the tapered middle, which element 24 consists of stainless steel and forms an extremely small electrolytically corrodible point. This advantageous embodiment is highly corrodible and therefore particularly well severed.

In FIG. 3c as an alternative a section of a micro-spiral 3 in accordance with the invention is illustrated with an essentially straight fitting 17 of stainless steel forming the electrolytically corrodible point 11, which fitting is fitted to the micro-coils 19 forming the electrolytically non-corrodible sections 10.

The disparities in electro-negativity between the stainless steel forming electrolytically corrodible points 11 and the platinum metal alloy forming the electrolytically non-corrodible sections 10 is, in an ionic medium, such as blood, responsible for the electrolytic severance of the electrolytically corrodible points 11 on the application of electrical power.

Figure 4:
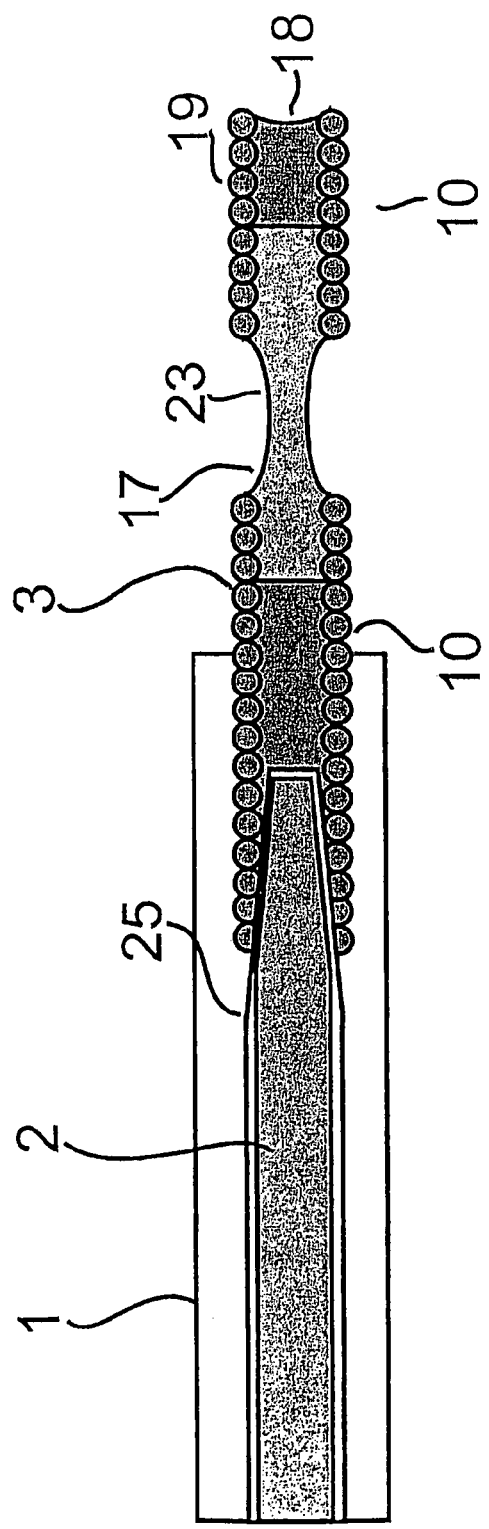
FIG. 4 shows a longitudinal section indicating the positioning of the guide wire (2) on the occluding spiral.

FIG. 4 shows a longitudinal section taken through the transition between the guide wire 2 and the occluding spiral 3 on a larger scale. In this example the guide wire 2 is constituted of high strength stainless steel and is surrounded by a coating 25, which prevents corrosion of the steel. This coating can either be made to be non-conductive, and in this case the electrical current for the end of the micro-catheter is conducted by the occluding spiral 3. Or the coating is non-corrodible but electrically conductive (for example a graphite coating), in which case the electric current may also be conducted via the guide wire 2 into the occluding spiral 3. In this example the occluding spiral 3 is formed by an arrangement of pre-corroded fittings 17 of stainless steel, which are attached mechanically by bonding in the inner space 18 by platinum micro-coils 19 forming electrolytically non-corrodible points. Fittings 17, pre-corroded intermediate the ends thereof, constitute particularly satisfactorily electrolytically corrodible points owing to their small diameter.

Figure 5:
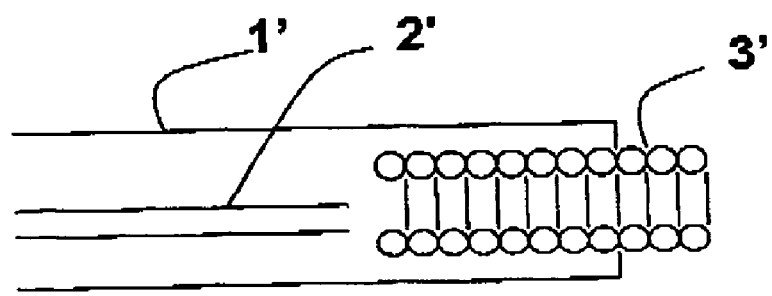
FIG. 5 Shows a longitudinal section indicating the positioning of a guide wire (2) on the occluding spiral that is formed as parts of the same wire.

FIG. 5 shows another embodiment in which a longitudinal section taken through the catheter 1', guide wire 2' and the occluding spiral 3' in which the guide wire 2' and the occluding spiral are manufactured in the form of parts of the same wire.

The invention claimed is:

1. A device for the implantation of occluding spirals able to be severed by electrolysis in body cavities or blood vessels comprising a source of electrical power, a cathode, a catheter and an occluding spiral adapted to serve as an anode and able to slide in the catheter in the longitudinal direction, the occluding spiral is designed to be electrolytically corrodible at a plurality of spaced apart points so that when in contact with a body fluid one or more variably dimensioned lengths of the occluding spiral may be severed by electrolysis, characterized in that the occluding coil is designed to be continuously electrically conductive in the proximal-distal direction.

2. The device as set forth in claim 1, characterized in that an insertion means, in the form of a guide wire, proximally adjoins the occluding spiral.

3. The device as set forth in claim 2, characterized in that the guide wire and the occluding spiral are joined together by soldering, brazing and/or bonding and/or welding operations and/or by mechanical connections.

4. The device as set forth in claim 2, characterized in that the guide wire and the occluding spiral are manufactured in the form of parts of the same wire.

5. The device as set forth in claim 1 or 2, characterized in that the occluding spiral or a part thereof is in the form of a micro-spiral.

6. The device as set forth in claim 1 or 2, characterized in that the occluding spiral or a part thereof is subject to a biasing stress and after release from the catheter forms coils.

7. The device as set forth in claim 1 or 2, characterized in that the electrolytically non-corrodible sections of the occluding spiral comprise one or more of the following materials: noble metals or noble metal alloys, corrosion-resistant ceramic materials, and corrosion-resistant plastics.

8. The device as set forth in claim 1 or 2, characterized in that the electrolytically corrodible points of the occluding spiral comprise one or more of the following materials: corrosion-resistant ceramic materials, corrosion-resistant plastics, and base metals or alloys thereof.

9. The device as set forth in claim 1 or 2, characterized in that AISI 301, 304 or 316 stainless steel are employed for the formation of the electrolytically corrodible points.

10. The device as set forth in claim 1 or 2, characterized in that for forming the electrolytically non-corrodible sections adjacent to transitions to the electrolytically corrodible points combinations of materials are selected which are suitable for forming local elements.

11. The device as set forth in claim 10, characterized in that the combinations of materials selected from groups consisting of the following are utilized:
   a) stainless steels for the formation of the electrolytically corrodible points with noble metals for the formation of the electrolytically non-corrodible sections;
   b) Ti or TiNi alloys for the formation of the electrolytically corrodible points with noble metals or noble metal alloys for the formation of the electrolytically non-corrodible sections;

c) Co based alloys for the formation of the electrolytically corrodible point with noble metal or noble metal alloys for the formation of the electrolytically non-corrodible sections.

12. The device as set forth in claim 5, characterized in that the points on the coils of the micro-spiral coil are shaped to be electrolytically corrodible points.

13. The device as set forth in claim 1 or 2, characterized in that the electrolytically corrodible points are on the micro-coils of the micro-spiral.

14. The device as set forth in claim 1 or 2, characterized in that the electrolytically corrodible points are aligned with the longitudinal axis of the occluding spiral.

15. The device as set forth in claim 1 or 2, characterized in that the electrolytically corrodible points are constituted by fittings which are fitted between the electrolytically non-corrodible sections of the occluding spiral.

16. The device as set forth in claim 1 or 2, characterized in that the fittings constituting the electrolytically corrodible points are joined to the electrolytically noncorrodible sections by soldering and/or brazing and/or bonding and/or welding operations and/or by mechanical methods.

17. The device as set forth in claim 1 or 2, characterized in that the electrolytically corrodible points are pre-corroded.

18. The device as set forth in claim 1 or 2, characterized in that the fittings constituting the electrolytically corrodible points are pre-corroded.

19. The device as set forth in claim 1 or 2, characterized in that the fittings are partly coated with a material, which is higher up in the electrochemical series than the material forming the fittings.

20. The device as set forth in claim 19, characterized in that the fittings consist of stainless steel and the coating consists of Zn, Zn alloys, Sn or Sn alloys.

21. The device as set forth in claim 15, characterized in that the fittings constituting the electrolytically corrodible points are micro-system components.

22. The device as set forth in claim 21, characterized in that the micro-system components contain micro-severance points as electrolytically corrodible points.

23. The device as set forth in claim 1 or 2, characterized in that the occluding spiral or a part thereof contains a continuous wire core of electrolytically corrodible material, which is surrounded by a casing repeatedly interrupted at intervals along the longitudinal axis and made of electrolytically corrosion resistant material.

24. The device as set forth in claim 1 or 2, characterized in that the diameter of the electrolytically corrodible points is between 0.01 and 0.05 mm.

25. The device as set forth in claim 1 or 2, characterized in that the end of the guide wire is provided with a coating preventing corrosion of the guide wire.

26. The device as set forth in claim 1 or 2 for methods used in veterinary or human medicine and preferably far thrombozation.

27. The device as set forth in claim 7 wherein the electrolytically non-corrodible sections of the occluding coil comprise platinum metal alloys.

28. The device as set forth in claim 8 wherein the electrolytically corrodible points of the occluding coil comprise stainless steel.

29. The device as set forth in claim 11 wherein the stainless steels are AISI 301, 304, 316 stainless steels.

30. The device as set forth in claim 11 wherein the noble metal combined with stainless steel is Pt or Pt metals, Pt alloys, Au alloys or Sn alloys.

31. The device as set forth in claim 11 wherein the noble metals or noble metal alloys combined with Ti or TiNi alloys are Pt, pt metals, Pt alloys, Au alloys or Sn alloys.

32. The device as set forth in claim 11 wherein the noble metals or noble metal alloys combined with Co based alloys are Pt, pt metals, Pt alloys, Au alloys or Sn alloys.

33. The device as set forth in claim 24 wherein the the diameter of the electrolytically corrodible points is between 0.02 and 0.04 mm.

34. The device as set forth in claim 24 wherein the the diameter of the electrolytically corrodible points is 0.03 mm.

* * * * *